US005741828A

United States Patent [19]
Stoy et al.

[11] Patent Number: 5,741,828
[45] Date of Patent: Apr. 21, 1998

[54] FLEXIBLE HYDROPHILIC COMPOSITE COATINGS

[75] Inventors: Vladimir A. Stoy, Princeton; Gerald A. Gontarz, Jr., Helmetta, both of N.J.

[73] Assignee: S.K.Y. Polymers, Inc., Rocky Hill, N.J.

[21] Appl. No.: 634,788

[22] Filed: Apr. 19, 1996

Related U.S. Application Data

[63] Continuation-in-part of Ser. No. 434,573, May 1, 1995, Pat. No. 5,688,855.

[51] Int. Cl.$^6$ ............................ C08J 3/02; C08L 33/20
[52] U.S. Cl. .................. 524/501; 524/523; 524/522; 524/521; 524/514; 524/507; 524/506; 524/565
[58] Field of Search ............................ 524/501, 523, 524/521, 522, 506, 507, 514, 565

[56] References Cited

U.S. PATENT DOCUMENTS

| 3,030,323 | 4/1962 | Turai | 524/501 |
| 4,923,920 | 5/1990 | Scholl et al. | 524/501 |

FOREIGN PATENT DOCUMENTS

| 8580 | 3/1971 | Japan | 524/501 |
| 162645 | 9/1983 | Japan | 524/501 |
| 81466 | 4/1987 | Japan | 524/501 |
| 1728262 | 4/1992 | Russian Federation | 524/501 |

*Primary Examiner*—Peter A. Szekely
*Attorney, Agent, or Firm*—Kenneth P. Glynn, Esq.

[57] ABSTRACT

The present invention is directed to a coating composition which includes a component A and component B. Component A is either an emulsion or dispersion having a hydrophobic elastomer stabilized with at lease one emulsifier. Component B is a dispersion or solution of a hydrophilic polymer which is insoluble in water, swellable in water and soluble in one or more water-miscible solvents. The hydrophobic elastomers may be polymers or copolymers of butadiene, isoprene, chloroprene, styrene, acrylonitrile, ethylene, propylene, isobutylene, alkylacrylates and alkylmethacrylates; polyrethanes, polyureas, polysiloxanes, elastomeric polyamides and polyesters. The hydrophilic polymers may be segmented polyurethanes, segmented polyures, segmented polyesters, partially hydrolyzed poly(vinyl acetate), partially hydrolyzed polyacrylonitrile, partially aminolyzed polyacrylonitrile, and ethylene glycol monomethacrylate. An optional Component C may be included which could be organic diluents and plasticizers; surfactants; water-soluble polymeric additives; inorganic or organic salts; pigments; fillers; biocides; UV-absorbers; preservatives; and particulate covalently cross-linked hydrogels.

16 Claims, No Drawings

FLEXIBLE HYDROPHILIC COMPOSITE COATINGS

REFERENCE TO RELATED APPLICATION

This application is a Continuation-in-Part of U.S. patent application Ser. No. 08/434,573, now U.S. Pat. No. 5,688,855 entitled "Thin Film Hydrophilic Coating" filed on May 1, 1995 by Vladimir A. Stoy, et al.

BACKGROUND OF THE INVENTION

1. Field of the Invention

The present invention involves coatings which have controlled properties of both hydrophobic and hydrophilic materials and may advantageously be used for coating articles which require both hydrophobic and hydrophilic properties.

2. Information Disclosure Statement

Many products require highly hydrophilic coatings with a low friction coefficient in the wet state, such as the hydrogel coatings which are described, for example, in U.S. Pat. No. 5,120,816 (F. Gould et al.), and No. 4,920,172 (S. Daoud), in European Patent No. 00993093B1, in British Patent No. 1,600,963 (Miclus et al.) and in European Patent No. 0166998B1 Terumo). In these applications, hydrogel coatings have to provide a good adhesion to the hydrophobic substrate while also providing high surface hydrophilicity. Those two contradictory requirements are solved in various ways. One of the recent solutions consists in the phase separation of hydrophilic and hydrophobic blocks in segmented copolymers with hydrophilic and hydrophobic moieties as described in the aforementioned parent U.S. application Ser. No. 08/434,573, incorporated herein by references. Even with the recent advances, hydrogel coatings have several disadvantages:

1) The hydrogel surface is often mechanically weak in the fully swelled state. This holds particularly true for very highly hydrated surfaces which are desirable for high slipperiness. The result is limited durability of such coatings and shedding of hydrogel fragments during use.

2) If only partially hydrated, hydrogels often form a surface with very high adhesion to themselves and to other materials. This problem of sticky semi-hydrated surfaces increases with increasing hydrophilicity of the hydrogel.

3) Hydrogel coatings are usually formed from compositions using flammable organic solvents or reactive components (such as initiators or cross linkers which are often toxic or irritating).

4) Hydrogels are often hard and brittle in their dry state. This problem is particularly difficult for thicker coatings (often preferable for applications requiring high slipperiness) and for coatings on elastic substrates (such as rubber).

5) Hydrogels stick readily to themselves if dried while in mutual contact. Such coatings often aggravate the self-adhesion problems typical of many elastomers (so called "blocking").

The present invention solves these problems by extending the concept of phase separation from solutions of polymer mixtures, used in the aforesaid co-pending parent patent application Ser. No. 08/434,573, to polymer dispersions and emulsions.

SUMMARY OF THE INVENTION

The present invention is directed to a coating composition which includes a component A and component B. Component A is either an emulsion or dispersion having a hydrophobic elastomer stabilized with at least one emulsifier. Component B is a dispersion or solution of a hydrophilic polymer which is insoluble in water, swellable in water and soluble in one or more water-miscible solvents. The hydrophobic elastomers may be polymers or copolymers of butadiene, isoprene, chloroprene, styrene, acrylonitrile, ethylene, propylene, isobutylene, alkylacrylates and alkylmethacrylates; polyurethanes, polyureas, polysiloxanes, elastomeric polyamides and polyesters. The hydrophilic polymers may be segmented polyurethanes, segmented polyureas, segmented polyesters, partially hydrolyzed poly (vinyl acetate), partially hydrolyzed polyacrylonitrile, partially aminolyzed polyacrylonitrile, and ethylene glycol monomethacrylate. An optional Component C may be included which could be organic diluents and plasticizers; surfactants; water-soluble polymeric additives; inorganic or organic salts; pigments; fillers; biocides; UV-absorbers; preservatives; and particulate covalently crosslinked hydrogels.

DETAILED DESCRIPTION OF THE PRESENT INVENTION

The present invention relates to the elastic hydrophilic coatings with low friction, good adhesion to non-polar substrates and good abrasion resistance in both dry and wet states. These coatings can be applied to surfaces of many materials (such as rubber, synthetic elastomers and plastics) to improve their friction and wettability as well as to eliminate their self-adhesion (blocking). The present invention coatings are created as water-born formulations and do not require use of any flammable or toxic components.

The coatings according to the present invention comprise the following components:

1) Component A: Aqueous emulsion or dispersion of an essentially hydrophobic elastomer stabilized with suitable emulsifiers (synthetic or natural "latex"; such dispersions, per se, are well known and widely used). The hydrophobic elastomers are polymers and copolymers of butadiene, isoprene, chloroprene, styrene, acrylonitrile, ethylene, propylene, isobutylene, alkylacrylates and alkylmethacrylates, polyurethanes, polyureas, polysiloxanes, elastomeric polyamides etc. The polymeric elastomers component is sterilized in the acqueous emulsions by a suitable emulsifiers, or a mixture of emulsifiers. The preferred type of emulsifiers are ionic emulsifiers, either alone or in a combination with one or more nonionic emulsifiers or non-surfactant dispersions stabilizers that are well known to those skilled in the art.

2) Component B: Solution or dispersion of a synthetic hydrophilic copolymer of the following properties:
   a) insoluble in water under ambient conditions;
   b) soluble in one or more water-miscible solvents;
   c) swellable in water under ambient conditions. The swelling in water should be higher than 33% by weight, and advantageously by more than 50% preferably 80% and most preferably 95%.

Typical examples of such compounds are polymers and copolymers of ethylene glycol monomethacrylate (PEGMA) that are soluble in alcohols and their aqueous solutions, but insoluble in water. While insoluble in water, PEGMA swells in water by more than 60% by weight. Particularly suitable for this purpose are segmented polymers with alternating hydrophilic and hydrophobic blocks capable of coagulation into soft gels. Since such coagulates lack the permanent covalent network typical for a hydrogel, their liquid content cannot be defined easily by the "equilibrium swelling"; it is often variable depending on conditions of coagulation, temperature and swelling history, etc. Segmented copolymers suitable for the present invention can be coagulated from their solutions into structures containing more than 80% of liquid, and frequently more than 95% of liquid. Such polymers are, for example, the segmented hydrophilic polyurethanes and polyureas with long polyethylene oxide chains described in the co-pending parent application cited above and incorporated herein by reference. Very suitable are, also, segmented hydrophilic polyesters with long polyethylene oxide chains and hydrophobic blocks comprising diesters of terephthalic acid; partially hydrolyzed polyvinyl acetate; partially hydrolyzed polyacrylonitrile, such as copolymers formed by hydrolysis of polyacrylonitrile according to U.S. Pat. No. 4,107,121 or U.S. Pat. No. 4,943,618 and segmented copolymers formed by partial aminolysis of polyacrytonitide described in U.S. Pat. No. 5,252,692.

The hydrophilic polymeric component is dissolved or dispersed in a suitable water-miscible liquid medium, preferably in an aqueous medium. Examples are water; aqueous solutions or organic and inorganic salts; lower aliphatic alcohols; acetone; DMSO; gamma-butyrolactone; DMF and their mixtures with water.

3) Optional component C: Additives such as are dissolved or dispersed organic diluents and plasticizers; surfactants; water-soluble polymeric additives; inorganic or organic salts; pigments; fillers; biocides; UV-absorbers; preservatives and the like. A particularly preferred additive is a finely particulate covalently cross-linked hydrogel, such as salts of cross-linked polyacrylic acid; copolymers of alkoxymonomethacrylates with alkoxydimethacrylates; cross-linked polysaccharides, such as starch or dextran; and the like.

Mixing of the above components creates a stable aqueous dispersion suitable for application onto the treated surface by dipping, painting, spraying and other usual methods. The components and mixing conditions have to be properly selected to achieve sufficient stability of the final formulation. It is often desirable to carry out the mixing gradually and under very low shear rate stirring.

The coating is formed by application of the formulation onto the coated surface, and by evaporating the volatile components of the formulation (primarily water). The coating properties can be favorably affected by drying at an elevated temperature, typically in the range between 25° C. and 95° C. The dry coated surface can be further stabilized by a heat treatment causing an additional phase separation, annealing or cross-linking of the polymeric components. Usual post-drying treatment temperatures are between about 100° C. and 160° C.

Resulting coatings have surface properties ranging from moderately hydrophilic to highly hydrated and slippery. The moderately hydrophilic surfaces have good mechanical properties and barrier properties of usual elastomers, the main difference being a more wettable surface that does not stick to itself (as many hydrophobic elastomers do). The highly hydrated surfaces are resistant to abrasion even in their wet state and are not sticky in their semi-dried state (as a hydrogel of similar slipperiness would). This allows the creation of a wide array of surfaces with hydrophilicity tailor-made for the desired application.

According to one present invention hypothesis, which is not to limit the scope of the invention in any way, the coating has a composite character. The elastomer of the component A always forms a continuous polymer phase while the hydrophilic polymers of the component B is separated from but partly adsorbed on the elastomer of the component A. It is postulated that the solid-gas interface is occupied primarily by the hydrophilic moieties of the component B rendering the surface hydrophilic. If the content of the hydrophilic polymer is low (between about 0.1% and 10% by weight on the dry substance of the coating), only the surface of the coating is hydrophilized while the excess of the hydrophilic polymer of the component B is embedded within the hydrophobic polymer forming more or less discrete domains.

At medium concentrations of the hydrophilic polymer (that is, above 10% but below about 33% by weight), domains of the hydrophilic polymer embedded within the hydrophobic matrix communicate mutually and with the surface of the coating. In the presence of a water excess, the hydrophilic domains swell and expand as to protrude partly from the surface so that the coating surface behaves as a hydrogel surface. In absence of water excess, the hydrophilic phase contracts due to drying and retracts into the hydrophobic matrix. Hence, even a semi-hydrated surface has properties of a dry elastomer. Very high concentrations of the hydrophilic components are not suitable for the present invention. If the concentration of the polymers in the component B exceeds about 35 to 40% of the dry weight, the surface layer weakens and expands by swelling and has some undesirable hydrogel-like properties. It is believed that at a higher concentration of component B above about 40% by weight, component A loses its continuous-phase character and the coating attains some hydrogel attributes that are undesirable for the present invention. It also should be noted that components B with lower hydrophilicity have to be added in higher concentrations to achieve the same final effect as the highly hydrophilic components present in a lower concentrations.

It is often advantageous to combine several different elastomers in component A to achieve some particular combination of properties. This can be readily achieved by mixing several mutually compatible dispersions of different polymers. Likewise, component B can contain several different hydrophilic polymers.

The formulations containing the component A, the component B and the optional component C may have between about 1% by weight and about 40% by weight of solids. The formulations with low solid concentrations (below about 5% by weight of solids) are suitable to form very thin coatings with excellent adhesion even on very elastic substrates, such as inflatable balloons.

The present invention is illustrated by the following non-limiting Examples:

EXAMPLE 1

A coating according to the present invention was prepared using a segmented polyurethane hydrogel as the hydrophilic polymer component and hydrophobic polyurethane elastomer in the rubber latex form as the hydrophobic polymer component.

Segmented polyurethane hydrogel is prepared by the following procedure: 61 grams of water is carefully added into 4.62 mol of methylene-bis(cyclohexyl4-isocyanate) (also known as Desmodur W, Miles Inc., Mobray Road, Pittsburgh, Pa.). The reaction of water with isocyanate groups forms amino groups and carbon dioxide, so that a mixture of the parent diisocyanate and methylene bis (cyclohexyl-4-amine) is formed (with some content of mono amine-monoisocyante derivatives).

The isocyanate-and amino groups react under forming urea blocks with an average molecular weight of about 3200 Daltons, terminated with isocyanate groups.

This mixture is added while stirring into a melt containing 1.06 mol polyethylene glycol of molecular weight 8000, 2.25 mol of diethylene glycol and 0.001 mol dibutyl dilauryltin.

The hot reaction mixture is poured onto a belt passing through a drying box heated to 105° C. The time of passage is about 30 minutes.

The resulting reaction mixture contains about 45% polymer and 55% of non-reacted mixture of diethylene glycol with polyethylene glycol. The mixture is insoluble in water and forms a firm hydrogel with about 85% of equilibrium-swelling water. The hydrogel is washed thoroughly with water to remove the major portion of the diethylene glycol and the polyethylene glycol.

This polymer is dissolved ethylalcohol to form 7% by weight solution. The solution is then diluted to 5% by weight of the polymer by slowly adding distilled water while stirring vigorously.

10 weight parts of the above 5% polymer solution was added to 70 weight parts of an aqueous polyurethane dispersion (available commercially as Sancure 1591® from B.F. Goodrich Company, Cleveland, Ohio, and containing 35% by weight of solids) and stirred vigorously for several minutes.

A film cast from this dispersion displays properties of both the hydrophobic elastomer (poor wetting with water, good adhesion to most surfaces in dry and wet state) and the hydrophilic component (partial swelling in water). The formulation is useful as a readily cleanable coating for areas that sustain oily spills or soiling by a grease.

EXAMPLE 2

A coating according to the present invention was prepared using poly (ethylene glycol monomethacrylate) (PEGMA) as the hydrophilic polymer component and natural rubber latex as the hydrophobic polymer component. PEGMA has been prepared in the following manner: 100 weight parts of ethylene glycol monomethacrylate (EGMA) is mixed into a mixture of 450 weight parts of ethylalcohol and 450 weight parts of water containing 1.5 weight parts of ammonium persulphate. The mixture is stirred under a nitrogen blanket and under reflux at 70° C. for 8 hours. A moderately viscous solution of poly (ethylene glycol monomethacrylate) (PEGMA) is thus formed. PEGMA is water insoluble but moderately swellable in water. A polymeric film formed by evaporation of the PEGMA solution swells to a soft, water-plasticized substance containing approximately 40% by weight of water. 100 weight parts of the PEGMA solution is gradually mixed into 500 weight parts of vigorously stirred diluted natural rubber latex with 10% by weight of solids. A small amount (0.25% by weight) of an anionic surfactant is added to the latex prior the mixing to increase stability of the resulting dispersion. The resulting dispersion is used to coat articles from natural rubber and other elastomers to eliminate their self-stickiness prior to chlorination.

EXAMPLE 3

A coating according to the present invention was prepared using partially hydrolyzed acrylonitrile copolymer (HPAN) as the hydrophilic polymer component and a butadiene-styrene copolymer in the latex form as the hydrophobic polymer component. The partially hydrolyzed PAN has been prepared in the following manner: 15 weight parts of a copolymer of acrylonitrile with 6% of methyl acrylate of molecular weight of 110,000 (weight average) is dissolved in 85 weight parts of cold 65% nitric acid. After the thorough dissolution, the temperature of the solution is increased to 23° C. and maintained for a time sufficient to hydrolyze approx. 80% of the present nitrile groups to a mixture of amide groups, carboxylic groups and a minor concentration of glutaroimide groups.

The aforesaid solution is then poured into a large excess of cold water. The copolymer coagulates to form a soft hydrogel with approx. 85% of water. The hydrogel including water is dissolved in DMSO to form a solution containing 5% by weight of the copolymer.

The butadiene-styrene latex is diluted to 5% by weight of solids and 0.5% by weight of a non-ionic surfactant is added. 100 weight parts of the DMSO solution is then gradually added to 400 weight parts of the diluted latex while stirring vigorously. Finally, 0.75 weigh part of cross-linked polyacrylic acid (Carbopol 934® by B.F. Goodrich Company, Cleveland, Ohio) is added adjust the dispersion viscosity. The formulation is applied to a non-polar surface and dried at 50° C. until looses its tackiness, then heated to 15° C. for another hour to complete the drying. The well wettable coating is useful, for instance, for inner surfaces of a centrifugal waste water pump to improve its performance and to decrease depositions of fatty substances.

EXAMPLE 4

A coating according to the present invention is prepared using partially hydrolyzed polyacrylonitrile (HPAN) as the hydrophilic polymer component and a mixture of butadiene-styrene copolymers in the latex form as the hydrophobic polymer component. The partially hydrolyzed PAN is prepared in the following manner: 10 weight parts of polyacrylonitrile (PAN) of molecular weight of 150,000 (weight average) is dissolved in 75 weight pares 55% by weight aqueous solution of NaSCN. Then 1.75 weight parts of NaOH, prediluted by 15 weight parts 55% by weight of the aqueous solution of NaSCN, is added to the PAN solution. The mixture is heated to 70° C. under nitrogen for 48 hours, then coagulated in a diluted aqueous methanol, washed in methanol and dried. The resulting copolymer is insoluble in cold water, but in forms a soft gel containing more than 99% of water under these conditions. 1 weight part of the dry copolymer is then dissolved in 200 weight parts of boiling distilled water.

Added to this are two commercially available water borne dispersions of Styrene-Alkylacrylic copolymers, one of a moderately low Glass Transition Temperature (Tg) and one of a higher Tg. This mixture is then diluted with water to the following composition (concentrations in weight percents):

0.2% of the HPAN copolymer
3.3% of the Pliolite 7217® (Goodyear Rubber a Tire Company, Acron, Ohio) dispersion of 45% by weight of a low-Tg Styrene-Acrylic copolymer in water
5.5% of the Carboset CR750® (B.F. Goodrich, Cleveland, Ohio) dispersion of 35% by weight of a high-Tg Styrene-Acrylic copolymer of water 91.0% Distilled Water The components form, upon a high-shear mixing, a homogeneous dispersion that dries to a dual layered coating due to the phase separation. The coating layer at the air/coating interface is a hydrophilic non-stick composition. The coating layer at the coating/substrate interface is an apparently homogeneous blend of the Styrene-Acrylic copolymers which provides excellent adhesion to variety of substances. This coating composition is useful for imparting a "tack-free", lubricious properties to otherwise self-sticking articles, such as rubber balloons, condoms or gloves.

What is claimed is:

1. A coating composition comprising:
   (a) Component A, being a composition selected from the group consisting of aqueous emulsions and dispersions, said composition containing an essentially hydrophobic constituent stabilized with at least one emulsifier; and
   (b) Component B, being a composition selected from the group consisting of solutions and dispersions, said composition containing hydrophilic polyacrylonitrile of the following properties:
      i) insoluble in water under ambient conditions;
      ii) soluble in one or more water-miscible solvents; and,
      iii) swellable in water under ambient conditions, said swelling in water being greater than 33% by weight of water when measured in its swelled state in water under ambient conditions.

2. A coating composition according to claim 1 wherein said hydrophobic constituent of Component A is selected from the group consisting of homopolymers and copolymers of butadiene, isoprene, chloroprene, styrene, acrylonitrile, ethylene, propylene, isobutylene, alkylacrylates and alkylmethacrylates; polyurethanes, polyureas, polysiloxanes, elastomeric polyamides and polyesters.

3. A coating composition according to claim 1 wherein said emulsifier is an ionic emulsifier.

4. A coating composition according to claim 1 wherein said hydrophilic polyacrylonitrile contains more than 50% of water by weight when measured in its swelled state in water under ambient conditions.

5. A coating composition according to claim 1 wherein said hydrophilic polyacrylonitrile contains more than 80% of water by weight when measured in its swelled state in water under ambient conditions.

6. A coating composition according to claim 1 wherein said hydrophilic polyacrylonitrile contains more than 95% of water by weight when measured in its swelled state in water under ambient conditions.

7. A coating composition according to claim 2 wherein said hydrophobic constituent contains more than one constituent set forth in the specified group.

8. The coating composition of claim 1 wherein said Component A is latex.

9. The coating composition according to claim 8 wherein said latex is a natural latex.

10. The coating composition of claim 8 wherein said latex is a synthetic latex.

11. A coating composition according to claim 1 wherein said hydrophilic polyacrylonitrile is partially hydrolyzed polyacrylonitrile.

12. A coating composition according to claim 1 wherein said hydrophilic polyacrylonitrile is a partially aminolyzed polyacrylonitrile.

13. A coating composition according to claim 1 wherein said composition also contains a Component C selected from the group consisting of organic diluents and plasticizers; surfactants; water-soluble polymeric additives; inorganic or organic salts; pigments; fillers; biocides; UV-absorbers; preservatives; and particulate covalently cross-linked hydrogels.

14. A coating composition according to claim 1 wherein said composition contains less than 10% of solids.

15. A coating composition according to claim 1 wherein said composition contains less than 33% of solids.

16. A coating composition according to claim 1 wherein said Component B contains a mixture of hydrophilic polyacrylonitrile polymers.

* * * * *